United States Patent
Kojima et al.

(10) Patent No.: US 6,916,858 B2
(45) Date of Patent: Jul. 12, 2005

(54) DENTAL ADHESIVE COMPOSITION

(75) Inventors: Shinichi Kojima, Tokyo (JP); Akishi Arita, Tokyo (JP)

(73) Assignee: GC Corporation, Tokyo (JP)

( * ) Notice: Subject to any disclaimer, the term of this patent is extended or adjusted under 35 U.S.C. 154(b) by 378 days.

(21) Appl. No.: 10/219,740

(22) Filed: Aug. 16, 2002

(65) Prior Publication Data

US 2003/0134934 A1 Jul. 17, 2003

(30) Foreign Application Priority Data

Aug. 30, 2001 (JP) ........................................ 2001-261943

(51) Int. Cl.$^7$ ........................ A61K 6/083; C08F 230/02; C08F 2/48
(52) U.S. Cl. ........................ 523/118; 523/120; 522/183; 526/277
(58) Field of Search ................................ 523/118, 120; 522/183; 526/277

(56) References Cited

U.S. PATENT DOCUMENTS

| | | |
|---|---|---|
| 5,089,051 A | 2/1992 | Eppinger et al. |
| 5,264,513 A | 11/1993 | Ikemura et al. |
| 5,834,532 A | 11/1998 | Yamamoto et al. |
| 5,925,690 A | 7/1999 | Fuchigami et al. |

FOREIGN PATENT DOCUMENTS

EP   1 066 813   1/2001

OTHER PUBLICATIONS

Patent Abstracts of Japan, JP 2001–072523, Mar. 21, 2001.

*Primary Examiner*—Tae H. Yoon
(74) *Attorney, Agent, or Firm*—Oblon, Spivak, McClelland, Maier & Neustadt, P.C.

(57) ABSTRACT

A one-pack type dental adhesive composition that does not require a pre-treatment such as an etching treatment and a priming treatment and can surely adhere a dental restoration material to a tooth structure and keep an adhesive effect over a long period of time, comprised of a polymerizable composition containing (a) 1~5% by weight of a polymerizable monomer containing a phosphoric acid group, (b) 10~40% by weight of a polymerizable monomer containing a plurality of carboxyl groups in one molecule, or being readily reactive with water to generate a plurality of carboxyl groups in one molecule, (c) 20~40% by weight of an acid group-free polymerizable monomer or a mixture of two or more acid group-free polymerizable monomers, both having a solubility of water at 25° C. of 25% by weight or less, and (d) 15~50% by weight of water, with (e) 0.1~5.0 parts by weight, based on 100 parts by weight of the polymerizable composition, of a photo-polymerization initiator and (f) a viscosity modifier having a mean particle size of 0.01~0.05 μm, the dental adhesive composition having a viscosity of 0.1~1 Pa·s.

16 Claims, No Drawings

DENTAL ADHESIVE COMPOSITION

BACKGROUND OF THE INVENTION

1. Field of the Invention

The present invention relates to a dental adhesive composition to be used for adhering a dental restoration material to a tooth structure. More particularly, the present invention relates to a one-pack type dental adhesive composition capable of surely adhering both of a dental restoration material and a tooth structure and keeping an adhesive effect over a long period of time through a simple operation in which a plurality of operation steps are not required during the use as in the conventional art and in which mixing of two or more multiple components are not required in one step, in case of adhering a dental restoration material such as filling composite resins, filling compomers, fissure sealants for pit and fissure block out, root coating materials, lining materials, and resin cements, to a tooth structure such as an enamel and a dentin.

2. Description of the Conventional Art

With spreading of dental restoration materials such as composite resins, dental adhesive compositions from which a strong adhesive effect is obtained through a simple operation are being demanded to adhere a dental restoration material to a tooth structure. With respect to the conventionally employed dental adhesive compositions and methods for using the same, is generally employed a method in which a tooth structure is etched with an acid such as phosphoric acid and citric acid, is then subjected to priming treatment with a primer containing an adhesive monomer or a hydrophilic monomer for enhancing the adhesive properties, and is further adhered by a bonding agent as an adhesive. However, this method was complicated in terms of the adhesion operation step because it requires three steps of etching treatment→priming treatment→bonding agent application treatment. Further, according to this method, though the adhesive properties to an enamel are high, it could not be said that the adhesive properties to a dentin are satisfactory.

In recent years, there was developed a two-step system in which the adhesion is carried out by using a self-etching primer, with which the etching treatment and the priming treatment can be carried out at the same time, and a bonding agent, that is, this two-step system is comprised of two steps of self-etching treatment→bonding agent application treatment. Also, recently, a one-step type adhesive composition that does not require a pre-treatment such as an etching treatment and a priming treatment but applies only a bonding agent application treatment is disclosed in Japanese Patent Laid-Open No. 2000-159621 and the like. However, since this adhesive composition basically acts as a primer, actually it requires a bonding agent separately. As described above, the currently commercially available two-step system type dental adhesive compositions or those that are in fact of a two-step system type but are called as a "one-step type" involved a defect that the operation is complicated.

Further, Japanese Patents Laid-Open Nos. 10-245525, JP-A-11-140383 and 2001-72523 propose one-step type adhesive compositions that do not require a pre-treatment such as an etching treatment and a priming treatment. However, in any of these cases, although these patents do not definitely describe, there was involved a defect that in order to obtain the required adhesive properties, a multiple components-mixing type catalyst is needed as a catalyst in addition to a photo-polymerization catalyst, and hence, two or more components must be in fact packed and stored separately from the standpoint of preservation stability. For this reason, the respective components must be mixed at the time of use, and though the adhesion operation itself is of a one-step system, the mixing operation is required at the time of use. Accordingly, there was a defect that the operation is complicated.

Moreover, Japanese Patent Laid-Open No. 2001-26511 discloses an adhesive composition comprising an acidic group-containing polymerizable compound, a water-soluble film-forming agent, water and a curing agent. This adhesive composition is of a one-pack type, which does not require a pre-treatment such as an etching treatment and a priming treatment. The film-forming agent containing 2-hydroxyethyl methacrylate as a major component, as used in this adhesive composition, is characterized in that it can be admixed with physiological saline water. However, such composition containing a large amount of a highly hydrophilic, polymerizable monomer such as 2-hydroxyethyl methacrylate involved a problem in durability. That is, when in actual clinics, the composition stays for a long period of time within an oral cavity, a polymer elutes out from a so-called hybrid (resin-impregnated) layer as a layer formed by polymerization and curing generated after highly hydrophilic polymerizable monomer component penetrates into a tooth structure, whereby leakage of edges and drop-out likely occur. In addition, it is worried about to use the composition containing a large amount of 2-hydroxyethyl (meth)acrylate from the standpoint of an allergy.

As discussed above, any dental adhesive composition which is practically useful and is of a one-pack type and that does not require a mixing operation during the use has not yet been obtained. Accordingly, a novel reliable dental adhesive composition whose operation is simple and which is stable in terms of an adhesive effect within an oral cavity over a long period of time has been demanded.

SUMMARY OF THE INVENTION

Thus, the present invention is aimed to provide a dental adhesive composition to be used for adhering a dental restoration material to a tooth structure, which does not require a pre-treatment such as an etching treatment and a priming treatment, can be used in one step of only an adhesion operation by a bonding agent application treatment, does not require mixing of two or more components at the time of use, and that can keep a high adhesive strength within an oral cavity over a long period of time.

We, the present inventors made extensive and intensive investigations to achieve the above-described aim. As a result, it has been found that with respect to a polymerizable composition capable of being processed in one step and comprising a polymerizable monomer containing a phosphoric acid group for enhancing adhesive properties to an enamel; a polymerizable monomer containing a plurality of carboxyl groups in one molecule, or being readily reactive with water to generate a plurality of carboxyl groups in one molecule, for enhancing adhesive properties to a dentin; an acid group-free polymerizable monomer having a low solubility of water for reinforcing an adhesive layer; and water for enhancing adhesive properties to a tooth structure, in order to obtain adhesive properties that have hitherto been considered to be impossible only by photo-polymerization and to reduce a content of a hydrophilic monomer such as 2-hydroethyl methacrylate, which is a cause of occurrence of elution of a polymer elute out from a hybrid layer, thereby generating leakage of edges and drop-out, when the foregoing components are compounded in a specific proportion, and the polymerizable composition is further compounded with a photo-polymerization initiator for polymerizing the various polymerizable monomers and a viscosity modifier having a mean particle size of 0.01~0.05 μm to adjust the viscosity at 0.1~1 Pa·s, it is possible to prepare a dental adhesive composition of a one-pack type, which does not require the mixing; that this dental adhesive composition has superior adhesive properties to a tooth structure and a dental restoration material; and that the polymerizable composition may contain a water-soluble, volatile organic solvent, leading to accomplishment of the present invention.

Specifically, the dental adhesive composition according to the present invention is a dental adhesive composition of a one-pack type, which comprises a polymerizable composition containing (a) 1~5% by weight of polymerizable monomer containing a phosphoric acid group, (b) 10~40% by weight of a polymerizable monomer containing a plurality of carboxyl groups in one molecule, or being readily reactive with water to generate a plurality of carboxyl groups in one molecule, (c) 20~40% by weight of a polymerizable monomer that is an acid group-free polymerizable monomer or a mixture of two or more acid group-free polymerizable monomers, having a solubility of water at 25° C. of 25% by weight or less, and (d) 15~50% by weight of water, having (e) 0.1~5.0 parts by weight, based on 100 parts by weight of the polymerizable composition, of a photo-polymerization initiator and (f) a viscosity modifier having a mean particle size of 0.01~0.05 μm further compounded therewith, the dental adhesive composition having a viscosity of 0.1~1 Pa·s.

The above-described polymerizable composition may additionally contain (g) 0.1~35% by weight of a water-soluble, volatile organic solvent. Also, as the polymerizable monomer containing a plurality of carboxyl groups in one molecule, or being readily reactive with water to generate a plurality of carboxyl groups in one molecule as the component (b) is preferred one kind or a mixture of two kinds of 4-(meth)acryloxyethyl trimellitic acid and 4-(meth)acryloxyethyl trimellitic anhydride.

DETAILED DESCRIPTION OF THE INVENTION

The polymerizable monomer containing the phosphoric acid group as the component (a), the polymerizable monomer containing a plurality of carboxyl groups in one molecule, or being readily reactive with water to generate a plurality of carboxyl groups in one molecule as the component (b) and the polymerizable monomer that is an acid group-free polymerizable monomer or a mixture of two or more acid group-free polymerizable monomers, having a solubility of water at 25° C. of 25% by weight or less as the component (c), each of which is used in the polymerizable composition of the dental adhesive composition according to the present invention, are each a polymerizable monomer of a methacrylate or an acrylate containing at least one unsaturated double bond in a molecule thereof.

The polymerizable monomer containing the phosphoric acid group as the component (a), which is used in the polymerizable composition of the dental adhesive composition according to the present invention, is a polymerizable monomer containing one or a plurality of phosphoric acid groups in one molecule. Since the phosphoric acid group exhibits a higher acidity than a carboxyl group, it is high in effects of dissolution of a smear layer of a tooth surface and dentinal decalcification and particularly, exhibits an improving effect for high adhesive properties to an enamel. Examples of the phosphoric acid group-containing polymerizable monomer as the component (a), which can be used in the present invention, include 2-(meth)acryloyloxyethyl dihydrogenphosphate, bis[2-(meth)acryloyloxyethyl] hydrogenphosphate, 2-(meth)acryloyloxyethylphenyl hydrogenphosphate, 6-(meth)acryloyloxyhexyl dihydrogenphosphate, 6-(meth)acryloyloxyhexylphenyl hydrogenphosphate, 10-(meth)acryloyloxydecyl dihydrogenphosphate, 1,3-di(meth)acryloyloxy-propane-2-dihydrogenphosphate, 1,3-di(meth)-acryloyloxypropane-2-phenyl hydrogenphosphate, and bis[5-{2-(meth)acryloyloxyethoxycarbonyl}heptyl]hydrogenphosphate. Of these is particularly preferred 10-(meth)acryloyloxydecyl dihydrogenphosphate from the standpoints of adhesive properties and stability of the monomer per se. These polymerizable monomer containing the phosphoric acid group may be used either singly or in admixture of two or more thereof. The polymerizable monomer containing the phosphoric acid group as the component (a) must be contained in an amount of 1~5% by weight in the polymerizable composition of the dental adhesive composition. When the amount of the polymerizable monomer containing the phosphoric acid group as the component (a) is less than 1% by weight, the adhesive properties to the enamel are weak, whereas when it exceeds 5% by weight, the adhesive properties to the dentin are lowered.

Since the carboxyl group present in the polymerizable monomer containing a plurality of carboxyl groups in one molecule, or being readily reactive with water to generate a plurality of carboxyl groups in one molecule as the component (b) has a milder action than a phosphoric acid group, is low in a danger of collagen modification of a dentin, and particularly, exhibits an improving effect for adhesive properties to the dentin. Examples of the polymerizable monomer containing a plurality of carboxyl groups in one molecule, or being readily reactive with water to generate a plurality of carboxyl groups in one molecule as the component (b), which can be used in the present invention, include 4-(meth)acryloxyethyl trimellitic acid, 4-(meth) acryloxyethyl trimellitic anhydride, 4-(meth)acryloxydecyl trimellitic acid, 4-(meth)acryloxydecyl trimellitic anhydride, 11-(meth)acryloyloxy-1,1-undecanedicarboxylic acid, 1,4-di(meth)acryloyloxy pyromellitic acid, 2-(meth) acryloyloxyethyl maleic acid, 2-(meth)acryloyloxyethyl phthalic acid, and 2-(meth)acryloyloxyethyl hexahydrophthalic acid. These polymerizable monomers containing a plurality of carboxyl groups in one molecule, or being readily reactive with water to generate a plurality of carboxyl groups in one molecule may be used either singly or in admixture of two or more thereof. Of these are particularly preferred 4-(meth)acryloyloxyethyl trimellitic acid and 4-(meth)acryloyloxyethyl trimellitic anhdyride from the standpoint of adhesive properties. The polymerizable monomer containing a plurality of carboxyl groups in one molecule, or being readily reactive with water to generate a plurality of carboxyl groups in one molecule as the component (b) must be contained in an amount of 10~40% by weight in the polymerizable composition of the dental adhesive composition. When the amount of the polymerizable monomer containing a plurality of carboxyl groups in one molecule, or being readily reactive with water to generate a plurality of carboxyl groups in one molecule as the component (b) is less than 10% by weight, the adhesive properties to the dentin are lowered, whereas when it exceeds 40% by weight, not only an improving effect for adhesive properties is not obtained, but also the polymerization properties of the dental adhesive composition per se become worse, whereby the adhesive properties to both the enamel and the dentin are lowered.

Examples of the polymerizable monomer that is an acid group-free polymerizable monomer or a mixture of two or more acid group-free polymerizable monomers, having a solubility of water at 25° C. of 25% by weight or less as the component (c), which can be used in the polymerizable composition of the dental adhesive composition according to the present invention, include methyl (meth)acrylate, ethyl (meth)acrylate, isopropyl (meth)acrylate, n-butyl (meth) acrylate, isobutyl (meth)acrylate, tetrahydrofurfuryl (meth) acrylate, glycidyl (meth)acrylate, 2-methoxyethyl (meth) acrylate, 2-ethylhexyl (meth)acrylate, benzyl (meth)

acrylate, 2,2-bis[(meth)acryloxyphenyl]propane, 2,2-bis[4-(meth)acryloxydiethoxyphenyl]propane, 2,2-bis[4-(meth)acryloxypolyethoxyphenyl]propane, ethylene glycol di(meth)acrylate, diethylene glycol di(meth)acrylate, triethylene glycol di(meth)acrylate, butylene glycol di(meth)acrylate, neopentyl glycol di(meth)acrylate, 1,3-butanediol di(meth)acrylate, 1,4-butanediol di(meth)acrylate, 1,6-hexanediol di(meth)acrylate, trimethylolpropane tri(meth)acrylate, pentaerythritol tri(meth)acrylate, trimethylolmethane tri(meth)acrylate, pentaerythritol tetra(meth)acrylate, 2-hydroxyethyl (meth)acrylate, 2-hydroxypropyl (meth)acrylate, 2-hydroxy-1,3-di(meth)acryloxypropane, 1,2-dihydroxy-3-(meth)-acryloxypropane, and 2,2-bis[4-{2-hydroxy-3-(meth)-acryloxypropoxy}phenyl]propane. Also, examples of acid group-free polymerizable monomers having a urethane bond in the molecule thereof include di-2-(meth)acryloxyethyl-2,2,4-trimethylhexamethylene dicarbamate.

The reason why, in the polymerizable monomer that is an acid group-free polymerizable monomer or a mixture of two or more acid group-free polymerizable monomers, having a solubility of water at 25° C. of 25% by weight or less as the component (c), the solubility of water at 25° C. must be 25% by weight or less is as follows. That is, in the case where the solubility of water at 25° C. exceeds 25% by weight, not only a problem occurs in the long-term durability of the so-called hybrid layer within an oral cavity, but also, since a large amount of the hydrophilic monomer such as 2-hydroxyethyl methacrylate is contained, the dentinal adhesive properties of the dental adhesive composition are lowered due to a poor polymerizability of the hydrophilic monomer per se.

In the dental adhesive composition according to the present invention, in order to make the permeability into a tooth structure and the polymerizability of the dental adhesive composition compatible with each other, it is preferred to mix the hydrophilic polymerizable monomer such as 2-hydroxyethyl methacrylate that contains a hydroxyl group with a polymerizable monomer having a good polymerizability, such as triethylene glycol dimethacrylate and di-2-methacryloxyethyl-2,2,4-trimethylhexamethylene dicarbamate, thereby adjusting the solubility of water at 25° C. to be 25% by weight or less.

The polymerizable monomer that is an acid group-free polymerizable monomer or a mixture of two or more acid group-free polymerizable monomers, having a solubility of water at 25° C. of 25% by weight or less as the component (c) must be contained in an amount of 20~40% by weight in the polymerizable composition of the dental adhesive composition. When the amount of the polymerizable monomer that is an acid group-free polymerizable monomer or a mixture of two or more acid group-free polymerizable monomers, having a solubility of water at 25° C. of 25% by weight or less as the component (c) is less than 20% by weight, the polymerizability of the dental adhesive composition becomes worse, whereby the adhesive layer cannot be reinforced, whereas when it exceeds 40% by weight, not only the permeability into the tooth structure becomes worse, but also, since the proportion in which the acid group-containing polymerizable monomer or water is contained is inevitably lowered, an etching effect is reduced, and the dentinal adhesive properties are lowered.

The water as the component (d), which is used in the polymerizable composition of the dental adhesive composition according to the present invention, is essential for making the polymerizable monomer containing the phosphoric acid group as the component (a) and the polymerizable monomer containing a plurality of carboxyl groups in one molecule, or being readily reactive with water to generate a plurality of carboxyl groups in one molecule as the component (b) act to effect dentinal decalcification and the like. As the water as the component (d), are preferred distilled water, purified water, ion-exchange water, and deionized water. The water as the component (d) must be contained in an amount of 15~50% by weight in the polymerizable composition of the dental adhesive composition. When the amount of the water as the component (d) is less than 15% by weight, the dentinal decalcification is weak, and the dentinal adhesive properties are lowered, whereas when it exceeds 50% by weight, the polymerization properties of the dental adhesive composition become worse, whereby the dentinal adhesive properties are lowered.

If desired, the polymerizable composition of the dental adhesive composition according to the present invention may be compounded with (g) a water-soluble, volatile organic solvent. Examples of the water-soluble, volatile organic solvent as the component (g), which can be used in the present invention, include acetone, methanol, ethanol, isopropyl alcohol, and methyl ethyl ketone. These water-soluble, volatile organic solvents may be used either singly or in admixture of two or more thereof. Of these are particularly preferred ethanol and acetone. When the water-soluble, volatile organic solvent as the component (g) is compounded in the polymerizable composition, it becomes easy to make the respective polymerizable monomers (a), (b) and (c) compatible with the water (d), thereby enabling to obtain a dental adhesive composition with high transparency. Further, even when the compounding amount of the water-soluble, volatile organic solvent as the component (g) is too short to achieve the compatibility, the dental adhesive composition can be supplied in an emulsified state. At this time, in the case where the emulsified state is unstable, it is preferred that, for example, spherical blocks such as alumina and zirconia are optionally charged into a container accommodating the dental adhesive composition, and before the actual use, the container is properly shaken and provided for the use. A suitable amount of the water-soluble, volatile organic solvent as the component (g) is 0.1~35% by weight in the polymerizable composition of the dental adhesive composition. When the amount of the water-soluble, volatile organic solvent as the component (g) is less than 0.1% by weight, the above-described effects are not obtained, whereas when it exceeds 35% by weight, the adhesive properties to the tooth structure are lowered.

In order that the adhesive interface and the adhesive layer are more strengthened, thereby enhancing the dentinal adhesive properties, it is necessary to have (e) a photo-polymerization initiator included in the dental adhesive composition according to the present invention. When the photo-polymerization initiator as the component (e) is further compounded in the polymerizable composition of the dental adhesive composition according to the present invention, thereby undergoing photo-polymerization, the adhesive properties can be thoroughly exhibited, and as a result, it becomes possible to obtain a one-pack type dental adhesive composition. As the photo-polymerization initiator as the component (e), which can be used in the present invention, are employable known photo-polymerization initiators that have hitherto been used for dental compositions. Examples thereof include α-diketone compounds, ketal compounds, anthraquinone-based compounds, thioxanthone-based compounds, benzoin alkyl ether-based compounds, acyl phosphine oxide-based compounds, and α-aminoketone-based compounds. Specific examples include camphorquinone, benzil, diacetyl, benzyl dimethyl ketal, benzyl diethyl ketal, benzyl di(2-methoxyethyl) ketal, 4,4'-dimethylbenzyl-dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diisopropylthioxanthone, 2-chloro-7-trifluoromethylthioxanthone, thioxanthone-10,10-dioxide, thioxanthone-10-oxide, benzion methyl ether, benzoin ethyl ether, benzoin isopropyl ether, benzoin isobutyl ether, benzophenone, bis(4-dimethylaminophenyl)ketone, 4,4'-bisdiethylaminobenzophenone, 2,4,6-trimethylbenzoyl diphenylphosphine oxide, 2,6-dimethylbenzoyl diphenylphosphine oxide, 2,6-dimethoxybenzoyl diphenylphosphine oxide, bis(2,4,6-trimethylbenzoyl)phenylphosphine oxide, and 2-methyl-1-[4-(methylthio)phenyl]-2-morpholinopropan-1-one. These photo-polymerization initiators may be used either singly or in admixture of two or more thereof. Of these are particularly preferred camphorquinone and 2,4,6-trimethylbenzoyl diphenylphosphine oxide. The photo-polymerization initiator as the component (e) must be compounded in an amount of 0.1~5.0 parts by weight based on 100 parts by weight of the polymerizable composition. When the amount of the photo-polymerization initiator as the component (e) is less than 0.1 parts by weight, the effects as the photo-polymerization initiator cannot be exhibited. On the other hand, even when it exceeds 5.0 parts by weight, the effects as the photo-polymerization initiator are no more improved. In addition, if desired, a photo-polymerization accelerator can be used in combination. For the photo-polymerization accelerator, an aromatic tertiary amine, an aliphatic tertiary amine, and the like are effective. Specific examples of the photo-polymerization accelerator that can be used include N,N-dimethyl-p-toluidine, N,N-diethyl-p-toluidine, N,N-dimethylaniline, N,N-bis(2-hydroxyethyl)-p-toluidine, N,N-dimethylaminoethyl methacrylate, triethanolamine, methyl 4-dimethylaminobenzoate, ethyl 4-dimethylaminobenzoate, isoamyl 4-dimethylaminobenzoate, triethylamine, N-ethyldiethanolamine, and triethanolamine. As a matter of course, these photo-polymerization accelerators may be used either singly or in admixture of two or more thereof.

For the purposes of making the adhesive layer intimate with the tooth surface and enhancing the strong dentinal adhesive properties, the polymerizable composition of the dental adhesive composition according to the present invention is compounded with a predetermined amount of (f) a viscosity modifier having a mean particle size of 0.01~0.05 μm. When the viscosity modifier having a mean particle size of 0.01~0.05 μm as the component (f) is compounded, there are brought effects such that the viscosity with which the control of the coating properties, fluidity of the dental adhesive composition and the thickness of the adhesive layer according to the present invention are greatly influenced, is adjusted and that the intimacy with a composite resin can be improved, thereby enabling to easily undergo the filling operation of the composite resin. In the case where the dental adhesive composition according to the present invention is supplied in an emulsified state, it is possible to make the emulsification more stable by compounding the viscosity modifier having a mean particle size of 0.01~0.05 μm as the component (f). As the viscosity modifier having a mean particle size of 0.01~0.05 μm as the component (f), are employable ultra fine inorganic fillers such as aerosil silica, aluminum oxide, and titanium dioxide. If desired, a silica glass powder, a barium glass powder, and the like may be used. Also, these viscosity modifiers may be provided for the use after subjecting to a silane coupling treatment. However, in this case, a glass powder having a reactivity with an acid, such as a fluoroaluminosilicate glass, cannot be used because it is reactive with the phosphoric acid group-containing polymerizable monomer as the component (a) or the polymerizable monomer containing a plurality of carboxyl groups in one molecule, or being readily reactive with water to generate a plurality of carboxyl groups in one molecule as the component (b).

The compounding amount of the viscosity modifier having a mean particle size of 0.01~0.05 μm as the component (f) greatly varies depending on the mean particle size and surface properties of the ultra fine inorganic filler and hence, cannot be unequivocally defined. Thus, the viscosity modifier having a mean particle size of 0.01~0.05 μm as the component (f) is compounded in the dental adhesive composition together with the polymerizable composition so that the viscosity of the whole of the dental adhesive composition is 0.1~1 Pa·s. When the viscosity of the dental adhesive composition is less than 0.1 Pa·s, the viscosity of the dental adhesive composition is low, the workability of the adhesion is poor, and the strength of the adhesive layer by the viscosity modifier cannot be expected so that the dentinal adhesive properties are lowered. On the other hand, when it exceeds 1 Pa·s, the dentinal permeability of the dental adhesive composition is poor so that the dentinal adhesive properties are lowered.

Besides, as a matter of course, the dental adhesive composition according to the present invention may be further compounded with trace amounts of a UV light absorber, a coloring agent, a polymerization inhibitor, etc., if desired.

The dental adhesive composition according to the present invention will be specifically described with reference to the following Examples, but it should not be construed that the present invention is limited thereto.

EXAMPLES 1 TO 6 AND COMPARATIVE EXAMPLES 1 to 4

Each of the components (a) to (d) as well as the components (f) and (g) was compounded in a compounding ratio as shown in Table 1 to prepare a one-pack type dental adhesive composition. Using this dental adhesive composition, the dentinal adhesive strength, the viscosity of the dental adhesive composition, and the solubility of water at 25° C. to the acid group-free polymerizable monomer were respectively measured. The results obtained are summarized and shown in Table 4. Here, the amount of the viscosity modifier having a mean particle size of 0.01~0.05 μm as the component (f) is shown based on 100 parts by weight of the polymerizable composition. Further, camphorquinone and isoamyl 4-dimethylaminobenzoate as the photo-polymerization initiator and the photo-polymerization accelerator as the component (e) were compounded in an amount of 0.5 parts by weight and 1.0 part by weight, respectively based on 100 parts by weight of the polymerizable composition.

(Dentinal Adhesive Strength)

1. The surfaces of fresh bovine anterior teeth were polished by a #600 waterproof polishing paper under pouring water so that five enamel surfaces and five dentin surfaces were exposed.

2. On each of the polished dentin surfaces or enamel surfaces was masked with a fluorocarbon resin-made tape provided with a hole having a diameter of 2.5 mm, thereby defining an adherent surface area. On the defined adherent surface, the dental adhesive composition of each of the Examples and Comparative Examples was applied without being subjected to etching and a priming treatment, kept for 20 seconds, and then dried by medium-pressure air, followed by irradiation with light for 10 seconds using a dental visible light irradiator (the product name: GC New Light VLII, manufactured by GC Corporation).

3. A silicone rubber-made mold having a height of 2.0 mm and provided with a hole having an inner diameter of 5.0 mm was placed on the adherent surface, and a photo-polymerization type composite resin (the product name: UniFil S, made by GC Corporation) was filled therein. Thereafter, the filled resin was cured upon irradiation with light for 40 seconds by the above-described dental visible light irradiator.

4. The test sample was immersed in water at 37° C. for one day, and an acrylic resin-made rod for tension was then installed in an upper portion of the test sample. Thereafter, the test sample was subjected to a tensile test by a universal tester (the product name: Autograph, manufactured by Shimadzu Corporation) at a cross-head speed of 1.0 mm/min.

(Viscosity of Dental Adhesive Composition)

The viscosity of the compounded dental adhesive composition was measured by a viscometer (the product name: MODEL DV-III, manufactured by Brookfield Engineering Laboratories). The measurement conditions are as follows. Spindle: SC4-14, temperature: 23° C., shear rate: 1/60 sec.

(Solubility of Water to Acid Group-free Polymerizable Monomer)

Ten grams of the mixture of acid group-free polymerizable monomers used in each of the Examples and Comparative Examples was collected into a sample tube, and a small amount of distilled water was added thereto step by step at 25° C. At the time when stirring had been carried out for one minute, it was visually observed whether the solution was clear or not. A concentration of water at the time when the solution had become clear was calculated and defined as a solubility of water to the acid group-free polymerizable monomer.

TABLE 1

| | Polymerizable composition | | | | | | | | (f) Viscosity modifier | | | | | |
|---|---|---|---|---|---|---|---|---|---|---|---|---|---|---|
| | (a) | (b) | | (c) | | | (d) | (g) | (part by weight) | | | | | |
| | MDP | 4-MET | HEMA | GDMA | TEGDMA | UDMA | Water | EtOH | OX50 | A50 | A200 | A380 | R972 | COK84 |
| Ex. 1 | 4 | 16 | 2 | 13 | 13 | 2 | 25 | 25 | 13 | | | | | |
| Ex. 2 | 4 | 16 | | 17 | 10 | 3 | 24 | 26 | | 10 | | | | 3 |
| Ex. 3 | 3 | 17 | | 15 | 15 | | 27 | 23 | | | 3.5 | | 3.5 | |
| Ex. 4 | 3 | 17 | 5 | 15 | 5 | 5 | 28 | 22 | | | | 4 | 4 | |
| Ex. 5 | 2 | 30 | | 15 | 5 | 10 | 22 | 16 | | 7 | | | | |
| Ex. 6 | 2 | 20 | 10 | 10 | 10 | | 38 | 10 | | | | 2.5 | 2.5 | |
| Com. Ex. 1 | 4 | 16 | 2 | 13 | 13 | 2 | 25 | 25 | 4 | | | | | |
| Com. Ex. 2 | 4 | 16 | | 17 | 10 | 3 | 24 | 26 | | 3 | | | | |
| Com. Ex. 3 | 3 | 17 | | 15 | 15 | | 27 | 23 | | | | | | |
| Com. Ex. 4 | 3 | 17 | 5 | 15 | 5 | 5 | 28 | 22 | | | | | | |

(Note)
MDP: 10-Methacryloyloxydecyl dihydrogenphosphate
4-MET: 4-Methacryloxyethyl trimellitic acid
HEMA: 2-Hydroethyl methacrylate
GDMA: 2-Hydroxy-1, 3-dimethacryloyloxypropane
TEGDMA: Triethylene glycol dimethacrylate
UDMA: Di-2-methacryloxyethyl-2,2,4-trimethylhexamethylene dicarbamate
EtOH: Ethanol
OX50: Aerosil OX50 (made by Nippon Aerosil Co., Ltd.)
A50: Aerosil 50 (made by Nippon Aerosil Co., Ltd.)
A200: Aerosil 200 (made by Nippon Aerosil Co., Ltd.)
A380: Aerosil 380 (made by Nippon Aerosil Co., Ltd.)
R972: Aerosil R972 (made by Nippon Aerosil Co., Ltd.)
COK84: Aerosil COK84 (made by Nippon Aerosil Co., Ltd.)

As compared with the dental adhesive compositions of Examples 1 to 6 according to the present invention, those of Comparative Examples 1 to 4 showed low values in the adhesive strength to an enamel and the adhesive strength to a dentin. These Comparative Examples 1 to 4 are an example where the viscosity modifier as in Examples 1 to 4 is not compounded, or only a small amount of the viscosity modifier is compounded. Any of the dental adhesive compositions of Comparative Examples 1 to 4 had a viscosity of less than 0.1 Pa · s.

Examples 7 to 12 and Comparative Examples 5 to 7: Using dental adhesive compositions each having a compounding ratio as shown in Table 2, various tests were carried out in the same test manners as in Example 1. The results obtained are summarized and shown in Table 4. Here, the type and compounding amount of each of the photo-polymerization initiator and the photo-polymerization accelerator are the same as in Example 1.

TABLE 2

| | Polymerizable composition | | | | | | | | | | | (f) Viscosity modifier | |
|---|---|---|---|---|---|---|---|---|---|---|---|---|---|
| | (a) | | | | (b) | (c) | | | | (d) | (g) | (part by weight) | |
| | MDP | PhenylP | PM21 | PM2 | 4-MET | HEMA | GDMA | TEGDMA | UDMA | Water | EtOH | A50 | COK84 |
| Ex. 7 | 3 | | | | 16 | | 17 | 10 | 3 | 25 | 26 | 7 | 4 |
| Ex. 8 | 2 | | | | 20 | 2 | 13 | 13 | 2 | 24 | 24 | 10 | 3 |
| Ex. 9 | | 2 | 1 | 1 | 16 | | 15 | 15 | | 25 | 25 | 10 | 12 |
| Ex. 10 | | | 2 | | 20 | 2 | 14 | 14 | | 24 | 24 | 9 | 3 |
| Ex. 11 | | | | 2 | 18 | | 15 | 5 | 10 | 22 | 28 | 12 | 1 |
| Ex. 12 | 1 | 1 | | | 20 | | 18 | 10 | 2 | 26 | 22 | 7 | |
| Com. Ex. 5 | | | | 2 | 20 | 25 | | 5 | | 30 | 18 | 10 | 3 |

TABLE 2-continued

| | | | | | | | | | | |
|---|---|---|---|---|---|---|---|---|---|---|
| Com. Ex. 6 | 2 | | 18 | 30 | | 10 | 10 | 30 | 9 | 3 |
| Com. Ex. 7 | 2 | | 18 | 15 | 2 | | 53 | 10 | 6 | 3 |

(Note)
MDP: 10-Methacryloyloxydecyl dihydrogenphosphate
PhenylP: 2-Methacryloyloxyethylphenyl hydrogenphosphate
PM21: Bis [5-{2-(meth)acryloyloxyethoxycarbonyl}heptyl] hydrogenphosphate
PM2: 2-Methacryoyloxyethyl dihydrogenphosphate
4-MET: 4-Methacryloxyethyl trimellitic acid
HEMA: 2-Hydroethyl methacrylate
GDMA: 2-Hydroxy-1,3-dimethacryloyloxypropane
TEGDMA: Triethylene glycol dimethacrylate
UDMA: Di-2-methacryloxyethyl-2,2,4-trimethylhexamethylene dicarbamate
EtOH: Ethanol
A50: Aerosil 50 (made by Nippon Aerosil Co., Ltd.)
COK84: Aerosil COK84 (made by Nippon Aerosil Co., Ltd.)

As compared with the dental adhesive compositions of Examples 7 to 12 according to the present invention, those of Comparative Examples 5 to 7 were low in the adhesive strength to an enamel and a dentin and were problematic in terms of the long-term stability within an oral cavity because the compounding amount of 2-hydroxyethyl methacrylate as the hydrophilic monomer is large and the solubility of water at 25° C. to the acid group-free polymerizable monomer exceeds 25% by weight.

Examples 13 to 17 and Comparative Examples 8 to 11: Using dental adhesive compositions each having a compounding ratio as shown in Table 3, various tests were carried out in the same test manners as in Example 1. The results obtained are summarized and shown in Table 4. Here, camphorquinone and 2,4,6-trimethylbenzoyl diphenylphosphine oxide as the photo-polymerization initiator were compounded in an amount of 0.5 parts by weight and 2.0 parts by weight, respectively based on 100 parts by weight of the polymerizable composition.

TABLE 3

| | Polymerizable composition | | | | | | | | (f) Viscosity modifier | | |
|---|---|---|---|---|---|---|---|---|---|---|---|
| | (a) | (b) | | (c) | | | (d) | (g) | (part by weight) | | |
| | MDP | 4-MET | HEMA | GDMA | TEGDMA | UDMA | Water | EtOH | A50 | A200 | R972 |
| Ex. 13 | 3 | 24 | | 24 | 5 | 10 | 34 | | 3 | | |
| Ex. 14 | 2 | 24 | | 15 | 5 | 10 | 34 | 10 | | 2 | 1 |
| Ex. 15 | 2 | 24 | 10 | 15 | 5 | 10 | 34 | | | 2 | 0.5 |
| Ex. 16 | 3 | 18 | | 24 | 5 | 10 | 40 | | 2 | 1 | 1 |
| Ex. 17 | 3 | 18 | | 15 | 5 | 10 | 44 | 5 | | 1 | 1 |
| Com. Ex. 8 | 3 | | | 39 | 8 | 16 | 34 | | 3 | 1 | |
| Com. Ex. 9 | | 24 | 10 | 15 | 5 | 10 | 36 | | | 2 | 0.5 |
| Com. Ex. 10 | 3 | 38 | | | | | 59 | | | 1 | 1 |
| Com. Ex. 11 | | | | 25 | 8 | 17 | 20 | 30 | | 3 | 3 |

(Note)
MDP: 10-Methacryloyloxydecyl dihydrogenphosphate
4-MET: 4-Methacryloxyethyl trimellitic acid
HEMA: 2-Hydroxyethyl methacrylate
GDMA: 2-Hydroxy-1,3-dimethacryloyloxy-propane
TEGDMA: Triethylene glycol dimethacrylate
UDMA: Di-2-methacryloxyethyl-2,2,4-trimethylhexamethylene dicarbamate
EtOH: Ethanol
A50: Aerosil 50 (made by Nippon Aerosil Co., Ltd.)
A200: Aerosil 200 (made by Nippon Aerosil Co., Ltd.)
R972: Aerosil R972 (made by Nippon Aerosil Co., Ltd.)

The dental adhesive compositions of Examples 13 to 17 according to the present invention were high in the adhesive properties to an enamel and to a dentin, and exhibited a superior adhesive strength. On the other hand, it is understood that the dental adhesive compositions of Comparative Examples 8 to 11 were low in the adhesive strength to a tooth structure due to lack of any of the components (a), (b) and (c) among the components (a), (b), (c) and (d) constituting the dental adhesive composition.

Comparative Example 12: A conventional dental adhesive composition (the product name: UniFil Bond, made by GC Corporation) was tested for the adhesive strength to an enamel and the adhesive strength to a dentin. This "UniFil Bond" is a two-step type dental adhesive composition composed of a self-etching primer and a bonding agent. The test for the adhesive strength was carried out in the following manner. That is, on each of the polished dentin surfaces or enamel surfaces was masked with a fluorocarbon resin-made tape provided with a hole having a diameter of 2.5 mm, thereby defining an adherent surface area. On the defined adherent surface, the self-etching primer was applied and dried by low-pressure air, and then the bonding agent was applied, followed by irradiation with light for 10 seconds by a dental visible light irradiator (the product name: GC New Light VLII, manufactured by GC Corporation). Thereafter, the operations 3 and 4 of the dentinal adhesive strength test as described above were carried out, thereby undergoing the test for the adhesive strength to a tooth structure. As described above, in this Comparative Example, the application operation of the self-etching primer and the drying operation by low-pressure air were necessary.

TABLE 4

| | Dentinal adhesive strength (MPa) | | Viscosity of adhesive (Pa · s) | Solubility of water to acid group-free polymerizable monomer (% by weight) |
|---|---|---|---|---|
| | To enamel | To dentin | | |
| Ex. 1 | 16.5 | 14.4 | 0.283 | 5.6 |
| Ex. 2 | 19.3 | 13.1 | 0.325 | 4.7 |
| Ex. 3 | 17.4 | 16.2 | 0.269 | 6.5 |
| Ex. 4 | 15.1 | 15.8 | 0.335 | 10 |
| Ex. 5 | 13.6 | 13.2 | 0.311 | 4.8 |
| Ex. 6 | 14.8 | 16.9 | 0.437 | 11 |
| Ex. 7 | 18.5 | 16.7 | 0.320 | 4.7 |
| Ex. 8 | 16.2 | 17.8 | 0.334 | 5.6 |
| Ex. 9 | 16.1 | 13.2 | 0.298 | 6.5 |
| Ex. 10 | 17.2 | 13.3 | 0.273 | 5.5 |
| Ex. 11 | 14.2 | 16.0 | 0.312 | 4.8 |
| Ex. 12 | 13.5 | 13.2 | 0.264 | 5.7 |
| Ex. 13 | 16.8 | 18.2 | 0.539 | 4.6 |
| Ex. 14 | 17.4 | 15.1 | 0.463 | 4.8 |
| Ex. 15 | 17.1 | 13.5 | 0.519 | 7.4 |
| Ex. 16 | 18.9 | 14.9 | 0.501 | 4.6 |
| Ex. 17 | 19.2 | 13.6 | 0.490 | 4.8 |
| Com. Ex. 1 | 7.3 | 7.4 | 0.042 | 5.6 |
| Com. Ex. 2 | 7.5 | 8.1 | 0.058 | 4.7 |
| Com. Ex. 3 | 4.3 | 5.7 | 0.0072 | 6.5 |
| Com. Ex. 4 | 5.2 | 6.4 | 0.0083 | 10 |
| Com. Ex. 5 | 6.1 | 8.8 | 0.219 | 50 |
| Com. Ex. 6 | 5.9 | 7.3 | 0.228 | 44 |
| Com. Ex. 7 | 8.1 | 9.9 | 0.256 | 58 |
| Com. Ex. 8 | 10.1 | 3.4 | 0.278 | 4.6 |
| Com. Ex. 9 | 4.5 | 11.4 | 0.510 | 7.4 |
| Com. Ex. 10 | 4.2 | 2.2 | 0.368 | — |
| Com. Ex. 11 | 0.2 | 0.8 | 0.322 | 4.8 |
| Com. Ex. 12 | 16.4 | 17.3 | | |

As described above in detail, the dental adhesive composition according to the present invention is a dental adhesive composition to be used for adhering a dental restoration material to a tooth structure, which does not require a pre-treatment such as an etching treatment and a priming treatment, can be used in one step of only an adhesion operation by a bonding agent application treatment, does not require mixing of two or more components at the time of use, and that can keep a high adhesive strength within an oral cavity over a long period of time. Accordingly, the present invention is greatly valuable in contributing to the dental remedy.

While the present invention has been described in detail and with reference to specific embodiments thereof, it will be apparent to one skilled in the art that various changes and modifications can be made therein without departing from the spirit and scope thereof.

What is claimed is:

1. A dental adhesive composition, which comprises a polymerizable composition comprising:
   (a) 1~5% by weight of a polymerizable monomer containing a phosphoric acid group,
   (b) 10~40% by weight of a polymenzable monomer containing a plurality of carboxyl groups in one molecule, or being readily reactive with water to generate a plurality of carboxyl groups in one molecule,
   (c) 20~40% by weight of a polymerizable monomer that is an acid group-free polymerizable monomer or a mixture of two or more acid group-free polymerizable monomers, having a solubility of water at 25° C. of 25% by weight or less, and
   (d) 15~50% by weight of water,
   (e) 0.1~5.0 parts by weight, based on 100 parts by weight of the polymerizable composition, of a photo-polymerization initiator and
   (f) a viscosity modifier having a mean particle size of 0.01~0.05 µm further compounded therewith, the dental adhesive composition having a viscosity of 0.1–1 Pa·s at a temperature of 23° C.

2. The dental adhesive composition according to claim 1, wherein the polymerizable composition further comprises (g) 0.1–35% by weight of a water-soluble, volatile organic solvent.

3. The dental adhesive composition according to claim 1 or 2, wherein the polymerizable monomer comprising a plurality of carboxyl groups in one molecule, or being readily reactive with water to generate a plurality of carboxyl groups in one molecule as the component (b) is selected from the group consisting of 4-(meth)acryloxyethyl trimellitic acid and 4-(meth)acryloxyethyl trimellitic anhydride, and mixtures thereof.

4. The dental adhesive composition according to claim 1, wherein (a) is selected from the group consisting of 10-methacryloyloxydecyl dihydrogenphosphate, 2-methacryloyloxyethylphenyl hydrogen-phosophate, bis(5-(2-(meth)acryloyloxyethoxycarbonyl)heptyl)hydrogen phosphate, 2-methacryoyloxyethyl dihydrogen phosphate, and mixtures thereof.

5. The dental adhesive composition according to claim 1, wherein (a) is 10-methacryloyloxydecyl dihydrogen phosphate.

6. The dental adhesive composition according to claim 1, wherein (a) is selected from the group consisting of 10-methacryloyloxydecyl dihydrogenphosphate, 2-methacryloyloxyethylphenyl hydrogen-phosophate, and mixtures thereof.

7. The dental adhesive composition according to claim 1, wherein (a) is selected from the group consisting of 2-methacryloyloxyethylphenyl hydrogen-phosophate, bis(5-(2-(meth)acryloyloxyethoxycarbonyl)heptyl)hydrogen phosphate, 2-methacryoyloxyethyl dihydrogen phosphate, and mixtures thereof.

8. The dental adhesive composition according to claim 1, wherein (a) is selected from the group consisting of bis(5-(2-(meth)acryloyloxyethoxycarbonyl)heptyl)hydrogen phosphate, 2-methacryoyloxyethyl dihydrogen phosphate, and mixtures thereof.

9. The dental adhesive composition according to claim 1, wherein (a) is 2-methacryoyloxyethyl dihydrogen phosphate.

10. The dental adhesive composition according to claim 1, wherein (c) is selected from the group consisting of 2-hydroxyethyl methacrylate, 2-hydroxy-1,3-dimethacryloyloxypropane, triethylene glycol dimethacrylate, di-2-methacryloxyethyl-2,2,4-trimethyl hexamethylene dicarbamate, and mixtures thereof.

11. The dental adhesive composition according to claim 1, wherein (c) is selected from the group consisting of 2-hydroxyethyl methacrylate, 2-hydroxy-1,3-dimethacryloyloxypropane, triethylene glycol dimethacrylate, and mixtures thereof.

12. The dental adhesive composition according to claim 1, wherein (c) is selected from the group consisting of 2-hydroxy-1,3-dimethacryloyloxypropane, triethylene glycol dimethacrylate, di-2-methacryloxyethyl-2,2,4-trimethyl hexamethylene dicarbamate, and mixtures thereof.

13. The dental adhesive composition according to claim 1, wherein (c) is selected from the group consisting of 2-hydroxy-1,3-dimethacryloyloxypropane, triethylene glycol dimethacrylate, and mixtures thereof.

14. The dental adhesive composition according to claim 1, wherein the water solubility of (c) at 25° C. is 10% by weight or less.

15. The dental adhesive composition according to claim 1, wherein said composition comprises 1–22% by weight of (f).

16. A dental restorative kit, comprising:

a package comprising the dental adhesive composition according to claim 1.

* * * * *